United States Patent
Bornemann

(10) Patent No.: US 9,610,430 B2
(45) Date of Patent: Apr. 4, 2017

(54) CELL SPRAYING DEVICE, METHOD AND SPRAYED CELL SUSPENSION

(71) Applicant: RenovaCare Sciences Corp., New York, NY (US)

(72) Inventor: Reinhard Bornemann, Bielefeld (DE)

(73) Assignee: RenovaCare Sciences Corp., New York, NY (US)

( * ) Notice: Subject to any disclaimer, the term of this patent is extended or adjusted under 35 U.S.C. 154(b) by 62 days.

(21) Appl. No.: 14/136,681

(22) Filed: Dec. 20, 2013

(65) Prior Publication Data

US 2014/0107621 A1   Apr. 17, 2014

Related U.S. Application Data

(63) Continuation of application No. 11/518,012, filed on Sep. 11, 2006, now abandoned.

(51) Int. Cl.
| | |
|---|---|
| A61B 17/00 | (2006.01) |
| A61M 37/00 | (2006.01) |
| A61M 35/00 | (2006.01) |
| A61B 19/00 | (2006.01) |
| A61F 5/44 | (2006.01) |
| A61M 31/00 | (2006.01) |

(52) U.S. Cl.
CPC ............ *A61M 37/00* (2013.01); *A61M 35/00* (2013.01); *A61B 2017/00969* (2013.01)

(58) Field of Classification Search
CPC ........... A61B 17/00; A61B 19/00; A61F 5/44; A61M 31/00
USPC .................................. 604/328, 406, 500, 20
See application file for complete search history.

(56) References Cited

U.S. PATENT DOCUMENTS

| | | |
|---|---|---|
| 5,139,031 A | 8/1992 | Guirguis |
| 5,571,083 A | 11/1996 | Lemelson |
| 5,810,885 A | 9/1998 | Zinger |
| 6,117,150 A | 9/2000 | Pingleton et al. |
| 6,479,052 B1 | 11/2002 | Marshall et al. |
| 7,628,780 B2 | 12/2009 | Bonner et al. |
| 7,641,898 B2 | 1/2010 | Lyles |
| 8,157,817 B2 | 4/2012 | Bonadio et al. |
| 8,529,957 B2 | 9/2013 | Turzi et al. |
| 8,790,680 B2 | 7/2014 | Chancellor et al. |

(Continued)

FOREIGN PATENT DOCUMENTS

| | | |
|---|---|---|
| DE | 19964113 A1 | 7/2001 |
| DE | 102007040252 A1 | 6/2008 |

(Continued)

OTHER PUBLICATIONS

Computer Desktop Encyclopedia, (1981).

(Continued)

*Primary Examiner* — Tatyana Zalukaeva
*Assistant Examiner* — Ilya Treyger
(74) *Attorney, Agent, or Firm* — Schwegman Lundberg & Woessner, P.A.

(57) ABSTRACT

The invention provides a device and methods suitable for producing a cellular spray of cells. The sprayed cells are of interest for covering and growing on a surface, including a skin wound. In applying the method and/or using the device, cells for grafting onto a patient are dispersed in a solution and sprayed with the device for distribution over the recipient's graft site.

11 Claims, 1 Drawing Sheet

(56) References Cited

U.S. PATENT DOCUMENTS

| | | | |
|---|---|---|---|
| 8,911,997 | B2 | 12/2014 | Upton et al. |
| 9,505,000 | B2 | 11/2016 | Bornemann |
| 2002/0082692 | A1 | 6/2002 | Van Blitterswijk et al. |
| 2002/0106353 | A1* | 8/2002 | Wood et al. ............... 424/93.7 |
| 2003/0202965 | A1 | 10/2003 | Seubert et al. |
| 2004/0043007 | A1* | 3/2004 | Andree et al. ............. 424/93.7 |
| 2004/0185091 | A1 | 9/2004 | Truong-le et al. |
| 2004/0219133 | A1 | 11/2004 | Lyles |
| 2005/0003524 | A1 | 1/2005 | Gerlach et al. |
| 2005/0003535 | A1 | 1/2005 | Gerlach |
| 2005/0015064 | A1 | 1/2005 | Gerlach et al. |
| 2005/0032218 | A1 | 2/2005 | Gerlach |
| 2006/0141616 | A1 | 6/2006 | Guu et al. |
| 2007/0042488 | A1 | 2/2007 | Bornemann |
| 2008/0038298 | A1 | 2/2008 | Barnikol-keuten et al. |
| 2009/0191631 | A1 | 7/2009 | Bornemann |
| 2009/0196855 | A1 | 8/2009 | Bornemann |
| 2009/0317439 | A1 | 12/2009 | Turzi et al. |
| 2013/0060335 | A1 | 3/2013 | Bornemann |
| 2015/0079153 | A1 | 3/2015 | Quick et al. |

FOREIGN PATENT DOCUMENTS

| | | | |
|---|---|---|---|
| DE | 102011100450 | A1 | 10/2012 |
| DE | 102011100450 | B4 | 7/2013 |
| DE | 102011100450 | B8 | 10/2013 |
| EP | 0809976 | A2 | 12/1997 |
| EP | 2049130 | A1 | 4/2009 |
| EP | 1664280 | B1 | 1/2011 |
| EP | 1357922 | B1 | 5/2011 |
| JP | 2005218376 | A | 8/2005 |
| WO | WO-02062358 | A1 | 8/2002 |
| WO | WO-2009017321 | A2 | 2/2009 |
| WO | WO-2013051816 | A2 | 4/2013 |
| WO | WO-2015078137 | A1 | 6/2015 |

OTHER PUBLICATIONS

Farlex Partner Medical Dictionary, (2000).
Saunders Comprehensive Veterinary Dictionary, (2000).
"U.S. Appl. No. 11/518,012, Final Office Action mailed Jun. 21, 2013", 15 pgs.
"U.S. Appl. No. 11/518,012, Non Final Office Action mailed Aug. 7, 2007", 9 pgs.
"U.S. Appl. No. 11/518,012, Notice of Non-Compliant Amendment mailed Jan. 29, 2013", 3 pgs.
"U.S. Appl. No. 11/518,012, filed Feb 28, 2013 to Notice of Non-Compliant Amendment mailed Jan. 29, 2013", 10 pgs.
"U.S. Appl. No. 11/518,012, filed Dec. 22, 2011 to Non Final Office Action mailed Aug. 7, 2007", 13 pgs.
"U.S. Appl. No. 13/573,003, Preliminary Amendment mailed Apr. 21, 2014", 7 pgs.
"Skin Cell Gun", Wikipedia, [Online]. Retrieved from the Internet: <URL: http://en.wikipedia.org/wiki/Skin_cell_gun>, (Accessed Apr. 22, 2014), 5 pgs.
Gerlach, "Skin Cell Gun", Poster, [Online]. Retrieved from the Internet: <URL: http://bethsumner.com/wp-content/uploads/2012/05/1338405697mmvrposterjpg>, (2012), 1 pg.
Gerlach, Jorg C, et al., "Method for autologous single skin cell isolation for regenerative cell spray transplantation with non-cultured cells", Int J Artif Organs 34(3), 271-279.

Hartmann, Bernd, et al., "Sprayed cultured epithelial autografts for deep dermal burns of the face and neck", Ann Plast Surg. 58(1), (2007), 70-73.
Herndon, David N, et al., "Comparison of cultured epidermal autograft and massive excision with serial autografting plus homograft overlay", J Burn Care Rehabil 13(1), (1992), 154-157.
Johnen, C., et al., "Skin cell isolation and expansion for cell transplantation is limited in patients using tobacco, alcohol, or are exhibiting diabetes mellitus", Burns, 32(2), (Mar. 2006), 194-200.
Navarro, F. A, et al., "Sprayed Keratinocyte Suspensions Accelerate Epidermal Coverage in a Porcine Microwound Model", Journal of Burn Care & Rehabilitation, 21(6), (Nov./Dec. 2000), 513-518.
"U.S. Appl. No. 13/573,003, Final Office Action mailed Feb. 18, 2016", 17 pgs.
"U.S. Appl. No. 13/573,003, Non Final Office Action mailed Jul. 22, 2015", 16 pgs.
"U.S. Appl. No. 13/573,003, filed Jan. 22, 2016 to Non Final Office Action mailed Jul. 22, 2015", 26 pgs.
"Respiratory Failure and Stimulation of Glycolysis in Chinese Hamster Ovary Cells Exposed to Normobaric Hyperoxia", The Journal of Biological Chemistry 265(19), (1990), 11118-11124.
Balin, Arthur K, et al., "Oxygen modulates growth of human cells at physiologic partial pressures", The Journal of Experimental Medicine 160(1), (Jul. 7, 1984), 152-166.
Goetz, Ingeburg E, "Oxygen Toxicity in Normal and Neoplastic Hamster Cells in Culture", Society for inn Vitro Biology 11(6), (1975), 382-394.
Kazzaz, Jeffery A, et al., "Cellular Oxygen Toxicity. Oxidant Injury Without Apoptosis", The Journal of Biological Chemistry 271(25), (1996), 15182-15186.
Michiels, Carine, et al., "Comparative Study of Oxygen Toxicity in Human Fibroblasts and Endothelial Cells", Journal of Cellular Physiology 144(2), (Aug. 1990), 295-302.
U.S. Appl. No. 15/360,230, filed Nov. 23, 2016, Device for Cell Spraying.
"U.S. Appl. No. 13/573,003, Examiner Interview Summary mailed Aug. 5, 2016", 3 pgs.
"U.S. Appl. No. 13/573,003, Notice of Allowance mailed Aug. 22, 2016", 8 pgs.
"U.S. Appl. No. 13/573,003, Notice of Allowance mailed Sep. 8, 2016", 5 pgs.
"U.S. Appl. No. 13/573,003, Response filed Aug. 3, 2016 to Final Office Action mailed Feb. 18, 2016", 10 pgs.
"Patents: WO2013051816 A2 (Google Translations)", Google, [Online]. Retrieved from the Internet: <URL:https://www.google.com/patents/WO2013051816A3?cl=en&dg=WO2013051816&hl=en&sa=X&ved=0ahUKEwj0hKap7MzRAhXCxlQKHUX6ABQQ6AEIFIDAA>, (Reterived: Jan. 18, 2017), 14 pgs.
"Patents: WO2015078137 A1 (Google Translation)", Google, [Online]. Retrieved from the Internet: <URL:https://www.google.com/patents/WO2015078137A1?cl=en&dg=WO2015078137&hl=en&sa=X&ved=0ahUKEwid_bjl68zRAhVhz1QKHQn_CwsQ6AEIGjAA>, (Reterived: Jan. 18, 2017), 7 pgs.
Wood, F. M, et al,, "The use of cultured epithelial autograft in the treatment of major bum wounds: Eleven years of clinical experience", Burns, 32(5), (2006), 538-544.
Wood, Fiona, "Clinical Potential of Autologous Epithelial Suspension", Wounds 15(1), (2003), 16-22.

* cited by examiner

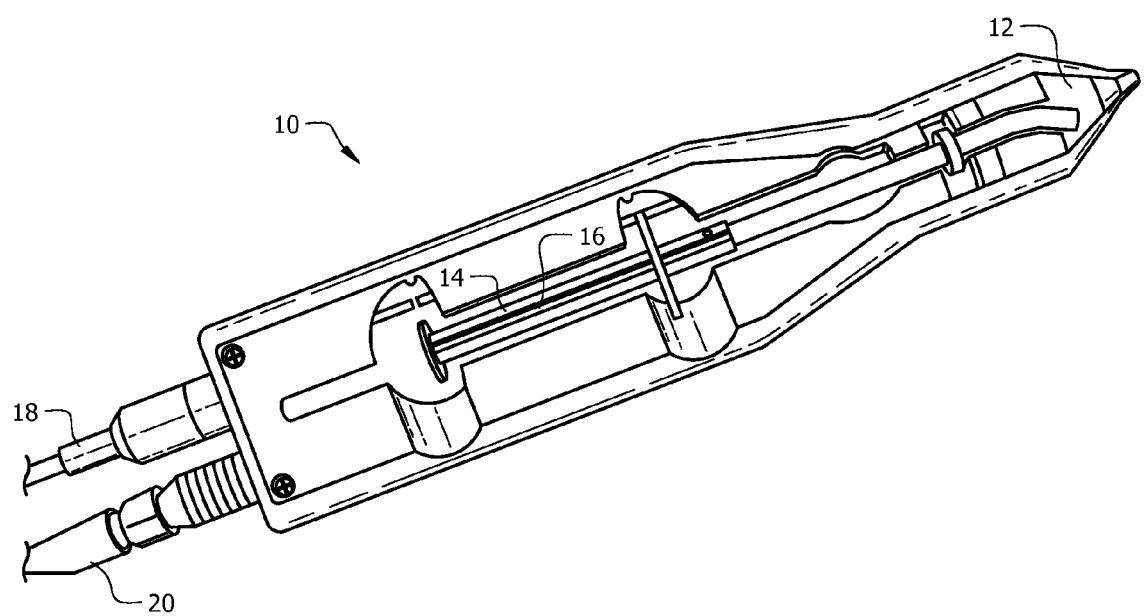

CELL SPRAYING DEVICE, METHOD AND SPRAYED CELL SUSPENSION

CROSS-REFERENCE TO RELATED APPLICATIONS

This nonprovisional application is a continuation of and claims priority to pending U.S. nonprovisional Application Ser. No. 11/518,012, entitled "Cell Spraying Device, Method and Sprayed Cell Suspension" filed Sep. 11, 2006 by the same inventor.

BACKGROUND OF THE INVENTION

1. Field of the Invention

This invention relates, generally, to the grafting of cells. In particular, it relates to a method of inducing epidermal growth and a device for spraying a cell suspension from a tissue sample obtained from a donor site and distributing that cell suspension to a recipient site, and its method of use thereof.

2. Brief Description of the Prior Art

Spraying of cells may be of interest for the distribution of cell suspensions onto a tissue wound. This can be applied, for example in general surgery to help regenerate tissue trauma. Methods for treating skin wounds are known. For example, skin grafting techniques exist, which aim to reconstruct skin areas of the body that have suffered either damage or defects to the skin. In general, these types of grafts are classified according to their host-donor relationship and by their thickness. The most clinically applied graft is the autologous graft, whereby tissue is taken from one area of the body and applied to another area. The grafted tissue then develops a new blood supply and attaches to the underlying tissues. There are several types of skin grafts presently used, including split-thickness, full-thickness grafts, and micro-grafting. Each of these graft types must be prepared using certain techniques, and each one has its inherent advantages and disadvantages. Split-thickness grafts often require considerable skill, time and expensive equipment. Further, donor sites are painful, result in scarring and limit the coverable area. Although split-thickness grafts may be more successful than full-thickness grafts, they are usually cosmetically less attractive. Full-thickness grafts require less skill and expensive equipment, and their cosmetic appearance is better than that of split-thickness grafts. However, full-thickness grafts do not "take" as well as split-thickness grafts. Micro-grafts are more easily accomplished and require no special instruments. However, their cosmetic appearance is not as good as other techniques, as the resulting scarring is unacceptable.

A variation to the above grafting techniques is the mesh graft, which is a type of split-thickness or full-thickness skin graft in which parallel rows of slits are cut into the treated tissue. Some of the advantages of mesh grafts include: greater coverage of the affected area, drainage of blood or serum from beneath the graft, and increased conformity of the graft to uneven recipient areas. This technique has been very successful, with 90 to 100 percent "take" after the grafts have been applied on healthy granulation beds.

An alternative to split-thickness grafting is to form a blister under suction at a donor site, then remove the skin above the blister and transplant it onto the recipient site. The production of blisters to treat wounds has been used since the 1960s. The blisters are produced by a suction device, such as DERMAVAC, at a suction pressure of approximately 250-300 mmHg for 1-2 hours. The blisters are then cut off and placed on the wound. The healing time is around 10-14 days. There are several disadvantages to this method, for example lengthy preparation of the graft and/or the graft itself potentially not resulting in re-pigmentation of the area; or the graft possibly resulting in uneven pigmentation around the edges of the area of treatment.

Micro-grafting has become a more common approach for large area cover and involves the "snipping off" of a number of very small sections of tissue from a donor site and applying them to a dressing that is in turn applied to the wound area.

Another technology for the generation of tissue in vitro is to culture epidermis. Cultured epithelial autografts (CEA), provided in confluent grown cell sheets, are an important adjunct in the coverage of burns and other situations in which large areas of the body's surface experience skin loss. There are many centers throughout the world with tissue culture facilities whose aim is to produce autologous epithelial grafts for use in a wide variety of applications. The usefulness and application of CEA is related to its ability to achieve confluent cells sheets suitable for grafting. This technique overcomes many of the disadvantages of the previous treatments described above. For example, cultured epithelial autografts reduce the demand for donor sites. However, these autografts are slow growing and require time to culture, which often exceeds the preparation time of the recipient's sites. Moreover, blister formation by wound secretion below the sheet grafts hinder grafting.

Navarro et al. (2000) and Wood et al. (2003) describe the use of single cells suspended in Hartmans's solution and distributed over the wound, thus avoiding the sheets. The cell suspension may be delivered via a pipette, common "eye-droppers," syringe and needle, and/or other similar devices to place small quantities of cellular suspension on a graft site. As method of choice a mechanical hand driven spray technique is described (see references).

The spray technique addressed some aforementioned problems in the field. A hand driven spray method and subsequent distribution of the cells, however, is not performed in a controlled manner and thus results in uneven cell distribution Accordingly, what is needed is an improved device and technique for skin grafting. However, in view of the prior art considered as a whole at the time the present invention was made, it was not obvious to those of ordinary skill in the art how the limitations of the art could be overcome.

While certain aspects of conventional technologies have been discussed to facilitate disclosure of the invention. Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved, more effective skin grafting device and solution is now met by a new, useful, and nonobvious invention.

The present invention provides a method and/or device suitable for producing a transplantable cellular spray of living cells suitable for grafting to a patient. In applying the method and/or in using the device, cells suitable for grafting to a patient are dispersed in a solution and sprayed with the device for distribution over the recipient graft site.

According to the invention a device and method is provided for spraying a cell suspension through a controlled spray head suitable for application to a patient utilizing a spray device, which method comprises the steps of: (a) subjecting a tissue sample including cells suitable for grafting to a patient, to at least a physical and/or chemical dissociating means capable of dissociating cells in the tissue sample; (b) taking the cells suitable for grafting on to a patient into a saline solution, (c) filtering the cellular suspension produced to remove large cellular conglomerates; and spraying the cell suspension through a spray head.

According to the invention an electronically controlled apparatus is provided as a medical device for distribution of tissue regenerating cells in a sterile suspension over a tissue surface via electronic controlled compressed gas and/or pump driven spraying through a sterilizeable spray head, providing continuous force application in a single shot and generating suspension drops containing cells.

According to the invention there is provided a cell suspension produced according to the above-described method. Preferably the cells in the suspension are autologous cells (i.e. they are isolated from the patient requiring an autograft), or stem cells.

According to another aspect of the invention a method is provided to treat a patient in need of graft surgery.

These and other aspects and advantages of the invention will become apparent to those skilled in the art from a review of the ensuing description, which proceeds with reference to the following descriptions and drawing.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWING

FIG. 1 depicts an embodiment of the current invention, containing uncultured autologous skin progenitor cells, which can be sprayed onto damaged skin tissue.

DETAILED DESCRIPTION OF THE PREFERRED EMBODIMENT

Those skilled in the art will appreciate that the invention described herein is susceptible to variations and modifications other than those specifically described, it is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification. Functionally equivalent products, compositions and where appropriate methods are clearly within the scope of the invention as described herein.

Throughout this specification and the claims that follow, unless the context requires otherwise, the word "comprise", or variations such as "comprises" or "comprising", will be understood to imply the inclusion of a stated integer or group of integers but not the exclusion of any other integer or group of integers.

Having regard to the above, certain embodiments of this invention provide a unique method and/or device suitable for producing a transplantable cellular suspension of living tissue suitable for grafting to a patient. In applying the method and/or in using the device cell preparations of different origin may be used. This includes stem cell preparations and patient autologous cells, whereas donor tissue is harvested and subjected to a tissue dissociating means. Cells suitable for grafting to a patient, or back to a patient, are dispersed in a solution that is suitable for immediate dispersion over the recipient graft site.

Certain embodiments of this invention have advantages over the prior art, some of which are described in the following paragraphs. The advantages set forth below and those made apparent from the following description are efficiently attained, and since certain changes may be made in the above construction without departing from the scope of the invention, it is intended that all matters contained in the following description or shown in the accompanying drawings shall be interpreted as illustrative and not in a limiting sense.

Certain embodiments of this invention provide a time efficient method for supplying a cellular cover to a tissue in a clinical setting. That is, cells can be finely and evenly distributed over a wound, avoiding the use of cell sheets. This is achievable because there is a controlled procuring of the cell suspension with a method provided by an apparatus, thus allowing cell spraying to be performed more evenly than conventional methods and devices for skin grafting.

Using individually-sprayed cells through an embodiment of the device disclosed here, rather than confluently grown keratinocyte sheets as in the prior art, results in the need for fewer cells and application to a larger treatment surface. Blister formation is avoided by the use of single cells without forming a closed sheet. Reducing the cell number speeds up application time by avoiding an in vitro cell expansion. Avoiding in vitro cell expansion, in turn, reduces in vitro differentiation and therefore better preserves basal keratinocyte progenitor cells in the cell suspension.

Certain embodiments of this invention aid in the achievement of rapid cell coverage in areas of tissue wounds, tissue trauma/injury and donor sites. It provides a means for reducing the size of skin cell donor sites—the biopsy donor site is markedly smaller than a split skin graft donor site and reduces or eliminates the use of split skin graft donor sites; improves the expansion rate of cell coverage; improves the rate of healing of small burns; is useful for small areas of skin reconstructions, such as scars; and improves scar quality, Certain embodiments of this invention provide a means for the treatment of various skin disorders or diseases. For example, the various skin disorders and diseases include, but are not limited to, the following: epidermal resurfacing, replacement after skin loss, site match-up during re-pigmentation of an area of skin, treatment of burn wounds, leukoderma, vitiligo, piebaldism, in the treatment of scars—for example, caused through incorrect wound healing, improper scar direction or scar distortion from wound contraction, acne scars; resurfacing cosmetic dermabrasion, resurfacing after laser treatment and in association with dermal reconstruction. Additionally the method may be used for cell replacement therapy, including but not limited to, nerve cell replacement treatment, epithelial cell (such as urothelial cell, buccal mucosal cell and respiratory epithelial cell) replacement treatment, endothelial cell replacement treatment and osteogenic precursor cell replacement treatment. The method may also be used to stimulate tissue regeneration in surgically induced wounds.

Certain embodiments of this invention provide a means to produce a suspension of cells in a ratio to each other comparable with those seen in situ. That is, due to the manner of preparation of the cellular suspension, cells such as keratinocyte basal cells, Langerhans cells, fibroblasts and melanocytes typically have enhanced survival rates in comparison to standard tissue culture techniques, whereby selective cell culture can result in the loss of certain cell types. This has the advantage of allowing for the correct re-pigmentation of skin after a skin graft.

Certain embodiments of this invention allow faster surgery and healing—thereby reducing trauma for patients during the phase of their medical care.

One embodiment of the invention relates to at least two distinct cell sources suitable for use in resurfacing and regeneration of damaged tissue: (i) non-autologous cells, including stem cells, and (ii) autologous cells, including the patient's own progenitor cells.

An embodiment of the invention provides a method for preparing an autologous cell suspension. According to this method, tissue is harvested from a patient by means known in the art of tissue grafting. Harvesting of tissue can be achieved by taking a tissue biopsy. With the harvesting of the biopsy consideration must be given to the depth of the biopsy and size of the surface area. The depth and size of the biopsy influence the ease at which the procedure can be undertaken and the speed with which a patient recovers from the procedure. The chosen donor site may appropriately match the recipient site, for example post-auricular for head and neck, thigh for lower limbs, inner-upper-arm for upper limbs, or palm for sole or vice-versa.

In this embodiment, once a biopsy has been harvested from a patient the tissue sample is subjected to physical and/or chemical dissociating means capable of dissociating cellular stratum in the tissue sample. Methods for dissociating cellular layers within the tissues are well known in the field. For example, the dissociating means may be physical and/or a chemical disruption. Physical dissociation means might include, for example, scraping the tissue sample with a scalpel, mincing the tissue, physically cutting the layers apart, or perfusing the tissue. Chemical dissociation means might include, for example, digestion with enzymes such as trypsin, dispase, collagenase, trypsin-edta, thermolysin, pronase, hyaluronidase, elastase, papain and pancreatin. Non-enzymatic solutions for the dissociation of tissue can also be used. Dissociation of the tissue sample may be achieved by placing the sample in a pre-warmed enzyme solution containing an amount of proteolytic enzyme sufficient to dissociate cellular stratum in the tissue sample.

After the tissue sample has been immersed in the enzyme solution for an appropriate amount of time, the sample can be removed and washed with nutrient solution.

In this embodiment, the saline/nutrient solution used in the method should be capable of significantly reducing or removing the effect of the enzyme either by dilution or neutralization. The nutrient solution used in the method may also have the characteristics of being (i) free of at least xenogenic serum, (ii) capable of maintaining the viability of the cells until applied to a patient, and (iii) suitable for direct application to a region on a patient undergoing tissue grafting. After application of a suitable saline/nutrition solution to the tissue sample, the cellular stratum of the sample is separated permitting the cells capable of reproduction to be removed from the cellular material and suspended in the nutrient solution. Where the tissue sample is skin, the dermis and epidermis can be separated to allow access to the dermal-epithelial junction of both surfaces.

In this embodiment, cells capable of reproduction are then removed from the separated stratum by any means known in the art. For example, the reproductive cells can be scraped off the surface of the stratum using an instrument such as a scalpel. Cells capable of reproduction within the dermal-epithelial junction include but are not limited to keratinocyte basal cells, Langerhans cells, fibroblasts and melanocytes. Following release of the cells from the tissue sample they are suspended in the saline/nutrient solution.

Another embodiment of the invention also provides a method for using a non-autologous cell suspension to produce cells capable of reproduction for purposes of skin grafting. To procure cells of any source, the cells are suspended in an aqueous saline/nutrition solution. The solution may be anything physiological from a basic salt solution to a more complex nutrient solution. Preferably, the nutrient solution is free of all serum but contains various salts, such as electrolytes, that resemble the substances found in body fluids; this type of solution is often called physiological saline. Phosphate or other non-toxic substances may also buffer the solution in order to maintain the pH at approximate physiological levels. Suitable nutrient solutions that are preferred base on Ringer-lactate solutions, including Hartmann's solution, dialysis solutions, and on peripheral intravenous nutrition solutions.

Whether using autologous or non-autologous sources, the volume of solution applied to the tissue sample after the harvesting steps, or by suspending non-autologous cells, may be small, otherwise the suspension may become too fluid therein providing difficulties in applying the suspension to the graft. The actual volume of solution applied will depend on the preference of the healthcare practitioner and the need of the patient.

In this embodiment, the cell suspension is then applied by using the spray device. To avoid excessively large cellular congregates in the cellular suspension the suspension can be filtered, either prior to using the suspension with the device, or by a specific feature of the device.

Prior to application with the device or immediately after filtering, the cellular suspension may be diluted to produce an appropriate cell density suitable for the purpose with which the suspension is to be used.

Embodiments of the invention also provide a sprayed aqueous cell suspension, highly suitable for tissue regeneration and grafting techniques, produced by the method described. An important advantage of the invention is an even cell distribution.

An important aspect of utilizing such a suspension in grafting technology is that it can be used to expand the area or volume of a wound that can be treated quickly by in situ multiplication of a limited number of cells. Cellular multiplication is encouraged on the patient rather than in an in vitro system, as provided by the conventional CEA method.

The number and concentration of cells seeded onto graft site may be varied by modifying the concentration of cells in suspension, or by modifying the quantity of suspension that is distributed onto a given area or volume of the graft site. The number and concentration of cells seeded onto the graft site depends on the preference of individual surgeons and the needs of the patient.

Another unique feature of the cell suspension that is contemplated is that the composition of cells in the cellular preparation is comparable to that seen in situ compared to prior art CEA cellular preparation. It contains the basal keratinocytes and skin progenitor cells for skin regeneration, which are typically lost in the CEA method. Whereas conventional methods lose cellular constituents, such as skin progenitor cells, because of selective culture for keratinocytes, the cellular suspension contemplated in the current invention has a cell composition comparable to the in situ cell population.

This invention also contemplates a method of treatment of the patient requiring a tissue graft. By this method the cellular suspension produced according to the invention is applied to a graft site.

This invention also contemplates an apparatus containing a spray head to distribute the cells. The suspension may be sprayed through any type of nozzle that transforms liquid into small airborne droplets.

An embodiment of the spray gun includes an electronically controlled apparatus used as a medical device to operate the spraying through a sterilizeable spray head. The apparatus enables a distribution of cells using about 0.5 to about 60±20 milliliter sterile cell suspension through a spray head. The apparatus can transfer the cell suspension from a medical grade disposable sterilizeable syringe, including about 0.5 to about 60 milliliter sterile Luer-lock syringes, or other secure syringes.

In this embodiment, the apparatus can be operated by producing a gas flow, for example air from a compressor, to engage the spray head, or forcing the cell suspension pump driven through the nozzle, for example by motor operated pushing of a sterile Luer-lock syringe containing the cell suspension, the gas may flow through a sterile syringe. An alternative is to produce the spray without mixing with gas. The apparatus also may provide continuous force application over a range of about 0.5 to about 10±1.0 minutes for a single shot, or several shots, and generate suspension drops containing cells in the range of about 30 to about 500±200 millimeters.

The apparatus may provide means to measure and control parameters such as flow, pressure, and/or temperature.

The apparatus may also transfer the cell suspension from a medical grade sterilizeable container to the sterilizeable spray head via a disposable filter capable of separating large cellular congregates from a cellular suspension. Any filter capable of separating excessively large cellular congregates from the suspension may be used. The filter may exhibits a cut off of about 5 cells to about 100 cells, preferably about 20 to about 60 cells and most preferably about 40 cells. The filter may cut off outside of these ranges, however noting that if the filter cuts off smaller cell aggregates, cells are lost for the patient, and if the filter cuts off larger cell aggregates, the system may clot.

An example of the spray gun is depicted in FIG. 1. The apparatus may comprise a first member, not shown, and second member 10 wherein: (i) the first member includes power supply, gas/air supply and electronic controls, and (i) the second member 10 includes a sterilizeable spray head 12 and a container 14 with the cell suspension 16. In that case both members may be connected through connectors 18, 20 which may be sterilizeable or can be covered with a sterile operation foil hose, not shown, and has suitable connectors to the first and second members. One connector may supply power and the other connector may supply gas/air from the power supply and gas/air supply within the first member, not shown, respectively. Examples of tangible connectors include, but are not limited to, cables, wires, tube sensors and effector connectors. The suspension is transformed into small airborne droplets by mixing the suspension with air/gas within the second member 10 when the container 14 is actuated to release the solution 16.

The apparatus may comprise a first and second member wherein both members are wirelessly connected for data exchange, including blue tooth technology, to connect sensor/effector controls in the first and second member.

The apparatus may also feature battery operation, facilitating an easy use in operation theaters. In that case, the apparatus comprises an all-in one device for hand-held operation.

After the cell suspension has been applied to the recipient graft site by the spray gun, the wound may be covered with a wound dressing. The healing of the wound is followed up by standard protocols for graft treatment.

In one embodiment, all materials were purchased from BIOCHROM AG, Berlin, Germany. Media were supplemented with antibiotics (Penicillin/Streptomycin, 120 μg/ml) and antimycotics (Amphotericin B, 2.5 μg/ml). A 1 cm$^2$ skin biopsy was obtained after obtaining informed consent of the donor and cut into 2 mm$^2$ pieces. Prior to separation of epidermis and dermis the pieces were exposed to 0.4% collagenase (Serva Electrophoresis GmbH, Heidelberg, Germany) in DMEM at 37° C. Separated epidermis was incubated with 0.05% trypsin/0.02% EDTA-solution for 15 minutes. The single cell suspension was cultivated in a standard culture flask with serum free culture medium (EPILIFE, TEBU, Offenbach, Germany). Cells were incubated at a cell density of $10^4$ per cm$^2$, using a CO2-incubator (HERAEUS BB 6060, Kendro, Langenselbold, Germany) at 37° C. in a humidified atmosphere with 5% $CO_2$. Medium was changed every two days. As 80% confluence was reached, cells were detached by trypsinization and used with the above described compressor operated spray gun. Operation parameters were set to an air flow of 3.7 l/min and a fluid flow of 4.2 cc/min. This adjustment resulted in a spray pressure of 8.2 mmHg. The cells were sprayed into anon medium filled standard cell culture dish at a density of $10^4$ cells per cm$^2$. As control cells from the same suspension were cultivated, under the above described culture conditions after pipetting into a medium filled culture flask with the same density. Cell morphology was monitored by light microscopy (ZEISS, AXIOVERT 25). Sprayed and non-sprayed cells showed similar morphologic appearance in light- and phase-contrast microscopy; they also showed comparable follow up culture behavior.

CITED SOURCES

Literature

NAVARRO F A, STONER M L., PARK C S, et al.: Sprayed keratinozyte suspensions accelerate epidermal coverage in a porcine microwound model, 2000, J. Burn Care & Rehabilitation, 21(6): 513-518.

WOOD F M: Clinical potential of autologous epithelial suspension, 2003, J. Wounds 15 (1): 16-22.

Wood F M, Allen P. The use of cultured epidermal autograft in the treatment of major burn injuries. J Burn Care Rehab 13(1) 2003:154-7.

Johnen C, Hartmann B, Steffen I, Brautigam K, Witascheck T, Toman N, Kuntscher MV, Gerlach JC. Skin cell isolation and expansion for cell transplantation is limited in patients using tobacco, alcohol, or are exhibiting diabetes mellitus. Burns. 2006;32(2):194-200.

US Patents/ Applications

U.S. Provisional Patent Application Serial No. 60/281,527, filed Apr.4, 2001

Foreign Application Data

Australian Provisional Patent Application PR 2989, Filled Feb. 7, 2001

Modifications and variations of the described methods and device of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant field in which this invention resides are intended to be within the scope of the described claims.

What is claimed is:

1. A method to treat a wounded area of skin on a human subject, comprising:
    providing a single cell-suspension of cells comprising progenitor skin cells in a serum-free physiological solution in a sterilizable container, wherein the cells are obtained from the subject's normal skin tissue that has been treated with enzymes so as to release the cells from the dermal-epithelial cell junction, wherein the skin cells have not been subjected to ex vivo or in vitro expansion;
    contacting the single-cell suspension of cells with a gas flow at an outlet of the container to create droplets of the suspension at a flow-controlled spray head; and
    spraying the droplets onto the wounded area of skin without forming a closed cell sheet so that the single cells are distributed directly and evenly and the cells regenerate normal skin by in situ multiplication to heal the wounded area in the absence of applying a preformed skin graft.

2. The method of claim 1 wherein the suspension comprises uncultured cell types in a ratio comparable to that found in normal skin.

3. The method of claim 1 or 2 wherein the cells comprise basal keratinocytes, Langerhans cells, fibroblasts and melanocytes.

4. The method of claim 1 wherein the cells in the suspension have a morphology that is similar to the cells in the droplets.

5. The method of claim 2 wherein the suspension comprises skin progenitor cells.

6. The method of claim 1, wherein the suspension is filtered to remove large cellular congregates.

7. The method of claim 6, wherein the filter has a cut-off of 5-100 cell congregates.

8. The method of claim 1 wherein the enzymes comprise dispase and trypsin.

9. The method of claim 1 wherein the enzymes comprise collagenase.

10. The method of claim 1 wherein the container is a syringe and the suspension is delivered to the outlet of the spray head by continuous force application to the container.

11. The method of claim 1 wherein the wounded area is burned.

* * * * *